United States Patent [19]

Serwer et al.

[11] Patent Number: 5,009,759
[45] Date of Patent: Apr. 23, 1991

[54] METHODS FOR PRODUCING AGAROSE GELS HAVING VARIABLE PORE SIZES

[75] Inventors: Philip Serwer; Gary A. Griess, both of San Antonio, Tex.

[73] Assignee: Board of Regents, The University of Texas System, Austin, Tex.

[21] Appl. No.: 411,373

[22] Filed: Sep. 22, 1989

[51] Int. Cl.$^5$ .................. G01N 27/26; B01D 57/02
[52] U.S. Cl. .................... 204/182.8; 204/299 R; 204/180.1
[58] Field of Search .............. 204/182.8, 299 R, 180

[56] References Cited

U.S. PATENT DOCUMENTS 3,527,712  9/1970  Renn et al. .................... 252/316

OTHER PUBLICATIONS

M. D. Biggin et al., "Buffer Gradient Gels and $^{35}$S Label as an Aid to Rapid DNA Sequence Determination", Proc. Natl. Acad. Sci. USA, vol. 80 (Jul. 1983), pp. 3963–3965.

Rodbard, D. et al., Anal. Biochem., vol. 40 (1971), 135–157.
Bothe, D. et al., Anal. Biochem., vol. 151 (1985), 49–54.
Fawcett, J. S. et al., Electrophoresis, vol. 10 (1989), 182–185.
Waki, S. et al., Biopolymers, vol. 21 (1982), 1909–1926.
Peats, S. et al., Biophysical Journal, vol. 49 (1986), 91a.
Griess, G. A. et al., Biopolymers, vol. 28, (1989), 1–10.
Sheen, J.-Y. et al, Biotechniques, vol. 6 (1988), 942–944.

*Primary Examiner*—John F. Niebling
*Assistant Examiner*—John S. Starsiak, Jr.
*Attorney, Agent, or Firm*—Arnold, White & Durkee

[57] ABSTRACT

Provided are agarose gels and processes for producing agarose gels having a uniform concentration of agarose and a pore size gradient. These gels are prepared by allowing gelation in a salt or buffer gradient. The agarose gels are suitable for the purposes of sieving based electrophoretic separations or other sieving-based separations, such as, chromatography.

59 Claims, 2 Drawing Sheets

Keep above gelation temperature to form gradient.
Insert comb to form wells.
Cool to set.

METHODS FOR PRODUCING AGAROSE GELS HAVING VARIABLE PORE SIZES

BACKGROUND OF THE INVENTION

The United States Government may have rights in this patent because of relevant developmental work supported by research grant no. DMB-8701379 from the NSF and grant no. GM24365 from the NIH.

Electrophoresis refers to the migration of charged solutes or particles in an electric field. Electrophoresis for macromolecule fractionation has been a valuable separation and quantitation technique in both the clinical and investigative laboratory. Electrophoresis can separate each type of molecule by zone. The zones are usually revealed by staining. Each zone appears as a visible band. One technique for electrophoretic separation is to pass a current through a buffer contained in a solid support medium. The support medium is typically constructed of cellulose, paper, cellulose acetate, starch gel, cross-linked dextran, polyacrylamide gel, or agarose gel. Molecules carrying an electric charge will move either to the cathode or to the anode of the electrophoretic system, depending on the nature of the charge of the molecule. The rate of movement of individual molecules is determined by: (1) net electric charge per surface area of the molecule; (2) size and shape of the molecule; (3) electric field strength; (4) nature and concentration of the supporting medium; and (5) the temperature of operation. For example, the speed of migration of a molecule increases as its average electrical surface charge density increases in magnitude (Shaw, D.J. (1969). Electrophoresis, Academic Press, London) and decreases as the molecules' motion is increasingly resisted by the support medium (reviewed in: Serwer, P. (1987). Biophysical characterization by agarose gel electrophoresis. In: New Directions in Electrophoretic Methods (Jorgenson, J.W. and Phillips, M., Ed.), Amer. Chem. Soc., Washington, D.C., pp. 158-166.). After electrophoresis, the current is terminated and the support medium is removed from the electrophoresis apparatus. The support medium may then be placed in a dye solution to stain the bands of solute macromolecules which have migrated into the support medium. The excess stain is then rinsed away. Quantitation of the solute macromolecule bands is generally achieved by using a densitometer. This instrument measures either the intensity of the light reflected from the dyed fraction (stained bands of solute macromolecules) or the amount of light transmitted through the support medium.

The basic method of electrophoresis, as set forth above, has been modified by investigators to suit particular purposes. For example, there are now specialized electrophoretic techniques, e.g., moving boundary electrophoresis, zone electrophoresis, immunoelectrophoresis, and isoelectric focusing electrophoresis. Each of these techniques is specifically designed to facilitate a desired type of separation. The present invention is directed toward the technique of using a porous support medium for the selective retardation during, for example, diffusion or electrophoretic migration, of solute macromolecules.

The capacity of certain porous support media to cause selective retardation based on either size or shape is well known. Such sieving media are used to separate biological macromolecules, i.e., proteins, DNA, RNA polysaccharides and the like. Such sieving media are characterized by the presence of a microporous structure which exerts a selective action on the migrating solute macromolecules, restricting passage of larger particles more than that of the smaller particles. Thus, the utility of sieving lies in the capacity of the sieving medium (support medium) to distinguish between molecules of different sizes and shapes. The porous support medium (sieving medium) is chosen to have a pore size appropriate for accomplishing the desired separation.

During electrophoresis, separations based on sieving have been achieved by using several sieving media including starch gel, cross-linked dextran, polyacrylamide gel, porous glass, agar gel, and agarose gel. It is known in the art that agarose forms gels useful in electrophoresis. Agarose gel electrophoresis has been successfully applied to the analysis of numerous biological macromolecules, for example, serum proteins, hemoglobin, lactate dehydrogenases, isoenzymes, lipoproteins, polynucleotides and the like. The versatility and convenience of agarose gels has made agarose the support medium of choice in some clinical and investigative laboratory settings.

The utility of agarose gels for either electrophoresis or other molecular sieving techniques, depends in part on the pore sizes achievable. According to U.S. Pat. No. 3,527,712, the pore size of agarose gel is dependent on the concentration of agarose in the gel. U.S. Pat. No. 3,527,712, states that gels with agarose concentrations greater than 5% have a porosity roughly comparable to that provided by cross-linked dextrans or polyacrylamide gels, in that while separation of smaller molecules can be achieved, it is not possible to effect separation between molecules of molecular weights greater than 200,000. However, it is known in the art that as the concentration of the agarose is decreased, the effective pore size of the gel is increased, and depending on a particular concentration of agarose, it becomes possible to effect molecular sorting of molecules having molecular weights greater than 200,000. The effective pore radius of agarose gels can be varied from 5 nm to 1-2 um (micrometers). The smaller radii are useful for procedures such as:

1. Sieving monomeric proteins (Easom, R.A., DeBuysere, M.S., Olson, M.S. and Serwer, P. [1989]; and
2. Size determination of multienzyme complexes using two-dimensional agarose gel electrophoresis (Proteins: Structure, Function and Genetics, 5, 224-232).

Gels with the larger pore radii are useful for procedures such as:

1. Sieving intact bacterial cells (Serwer, P., Moreno, E.T. and Griess, G.A. [1988];and
2. Agarose gel electrophoresis of particles larger than 100 nm: Fractionation of intact *Escherichia coli*. (Electrophoresis '88, Schafer-Nielsen, C., Ed. pp. 216-222).

This ability to control the pore size of agarose gels is greater than anything known with gels of other compounds.

Typically, molecular sieving media, as discussed above, have a uniform mean pore size throughout. However, it becomes apparent that a sieving medium having a plurality of pore sizes, arranged in a gradient, could effectively: (a) fractionate particles with a greater range of sizes, (b) sharpen the bands formed by particles of unique size, and (c) cause effective cessation of motion based on pore size. Thus, other investigators in the art have attempted to manufacture sieving media having a gradient of pore size, for example, polyacrylamide and agarose gels.

With respect to polyacrylamide gels, a pore size gradient was created by pouring a concentration gradient of acrylamide before polymerization and subsequent gelation of the acrylamide (Rodbard, D., Kapadia, G. and Chrambach, A. (1971). Pore gradient electrophoresis. Anal. Biochem. 40, 135-157. Bothe, D., Simonis, M., and von Dorhen, H. (1985), A sodium dodecyl sulfate-gradient gel electrophoresis system that separates polypeptides in the molecular weight range of 1500 to 100,000. Anal. Biochem. 151, 49-54. Fawcett, J.S., Sullivan, J.V. and Chrambach, A. (1989). Toward a steady-state pore limit electrophoresis dimension for native proteins in two-dimensional polyacrylamide gel electrophoresis. Electrophoresis 10, 182-185.). The pore size decreases as the concentration of gel increases. The pore size gradient has the largest pores at the origin of electrophoresis. This procedure usually requires about an hour per gradient pouring. In addition, reproducing defect-free gradients is difficult, in part because of the difficulty in reproducing pouring conditions. Because agarose must be maintained at 50 to 60° C., the concentration gradients are more difficult to pour than concentration gradients of other gel-forming compounds. However, the many advantages and uses of agarose gels having a gradient of pore size have provided a strong incentive to develop new and x improved methods for producing them. For e ample, the use of agarose gels having a pore size gradient is desirable for: (a) increasing the sharpness of bands, (b) extending the range of molecules separated; and (c) performing steric exclusion electrophoresis by pore size exclusion.

Waki et al. (Biopolymers 21 1909-1926, 1982) have studied agarose gel structure by electron microscopy of freeze-fractured surfaces and noted that gels set in the presence of salt have larger interfiber spaces and greater pore size. This larger pore size was confirmed by electrophoretic measurements of relative migration rates for plasmid DNA molecules of varying conformations. Peats et al. (Biophysical Journal 49 91a, 1986) reported finding that agarose gelled in the presence of borate had an increase in sieving power.

Accordingly it would be advantageous to develop a agarose gel having a gradient of pore size without the expense and problems typically associated with prior attempts based on agarose concentration gradients. Moreover, it would be advantageous to produce an agarose gel having a gradient pore size which could be simply and inexpensively manufactured for use in clinical and investigative laboratories. For maintaining uniformity of thickness during post-electrophoresis drying, a pore gradient formed at uniform gel concentration is superior to a pore gradient formed by varying the gel concentration. Drying is performed for autoradiography and fluorography. Thus, the methods of the present invention are particularly directed to agarose gels having a uniform agarose concentration and a pore-size gradient, pore size decreasing with increasing distance from the origin of electrophoresis, as well as methods for producing such agarose gels. The present inventors have determined that the pore size of an agarose gel may be effectively controlled by varying the composition of the buffer during gelation. Thus, unlike the prior art in this field, the present invention demonstrates production of an agarose gel having a pore size gradient, not by varying the concentration of the agarose in the gel, but by varying, during gelation, the buffer (or non-buffering ion) composition in different regions of the gel.

SUMMARY OF THE INVENTION

The present invention demonstrates herein that the pore size of an agarose gel can be directed by controlling the buffer or salt concentration of an agarose solution during gelation.

An important aspect of the present invention is directed toward a method for controlling the pore size of an agarose gel. In one embodiment, this method includes the steps of:

(a) preparing aqueous solutions of agarose having different salt and/or buffer concentrations; and (b) gelling said solutions in proximity to each other.

The present invention is also directed to agarose gels which may have a uniform agarose concentration and a pore size gradient and processes for producing such agarose gels. Both vertical and horizontal gel molds may be utilized in separate aspects of the invention.

In a vertical gel mold, a preferred process comprises the steps of:

(a) preparing a plurality of buffered aqueous agarose solutions, each solution including an identical concentration of agarose and a different molar concentration of a buffer or salt, said molar concentration of said buffer or salt determining the pore size of the gelled agarose; and (b) adding, sequentially, in order of decreasing buffer or salt molar concentration, the aqueous agarose solutions to said vertical gel mold prior to gelation. It should be noted that the agarose concentrations may be the same but need not be to form a pore gradient.

In a horizontal gel mold, a preferred process comprises the steps of:

(a) dividing said horizontal gel mold into a first and second compartment by dividing means;

(b) preparing a first aqueous agarose solution having a first buffer or salt concentration;

(c) pouring this aqueous agarose solution into the first compartment;

(d) removing, said dividing means after gelation of the first aqueous agarose solution.

(e) preparing a second aqueous agarose solution, this solution having a second buffer or salt concentrations being lower than the first;

(f) pouring said second aqueous agarose solution into the second compartment;

(g) keeping the second agarose gel above the gelation temperature until diffusion of salt or buffer has formed a salt or buffer gradient; and (h) lowering temperature to allow gelation of the second solution.

The agarose gels of the present invention are useful in separating, by means of sieving (hydrodynamic or steric), molecules by size, shape or molecular weight. Typically, these molecules are molecules such as: endonuclease-resisted DNA and RNA fragments, proteins, multimolecular protein complexes and the like. Several techniques based on sieving may be utilized in conjunction with the agarose gels of the present invention, for example, gel electrophoresis, and molecular sieve chromatography.

BRIEF DESCRIPTION OF THE DRAWINGS

FIG. 2 also illustrates the resultant gradient of buffer concentration.

DESCRIPTION OF THE PREFERRED EMBODIMENTS

The present invention provides a process for producing novel agarose gels which may have a uniform concentration of agarose and do have a pore size gradient. The agarose gels of the present invention are useful for several sieving-based techniques, i.e., electrophoresis, chromatography and the like. The agarose gels of the present invention may be used, for example, to detect, fractionate, concentrate, quantify and qualify samples, specimens or complex proteins of biological or commercial origin. Such studies include those directed to complex mixtures, including: lesions of atherosclerosis; sera; cellular extracts; nuclear extracts (chromosomal DNAs). The sensitivity of detection of such isolates beyond that achievable by prior art techniques represents a significant advantage of the present invention.

One embodiment of the invention is directed toward a process for controlling the pore size of an agarose gel. This process includes several steps. One step of the inventive process is the preparation of an aqueous solution of agarose. According to one preferred embodiment, from about 0.5 to about 5% agarose is boiled in water.

Another step in the inventive process is adding to the aqueous agarose solution prior to gelation a sufficient amount of either a buffer or a non-buffering salt to achieve a predetermined molar concentration. One may dissolve the agarose in a pre-selected buffer or salt solution if desired. It has been determined that the concentration of the buffer or salt in the agarose solution determines the pore size of the gelled agarose. According to one preferred embodiment, the concentration of salt and/or buffer is from about 0.00 M to about 0.5 M. However, most preferably, the molar concentration is from about 0.01 M to about 0.20 M. The buffer or salt of the present invention is preferably at least one selected from the group consisting of potassium dihydrogen phosphate, disodium hydrogen phosphate, tris(hydroxymethyl)aminomethane, sodium bicarbonate, sodium acetate, and sodium tetraborate although many other buffers may be used. However, it should be noted that any buffer which disassociates at a pH of from about 6.0 to about 8.0 and does not precipitate with agarose may be utilized in the practice of the present invention. Examples of salts known to be usable include sodium chloride potassium chloride and calcium chloride but many other salts may be utilized.

Figure 4:
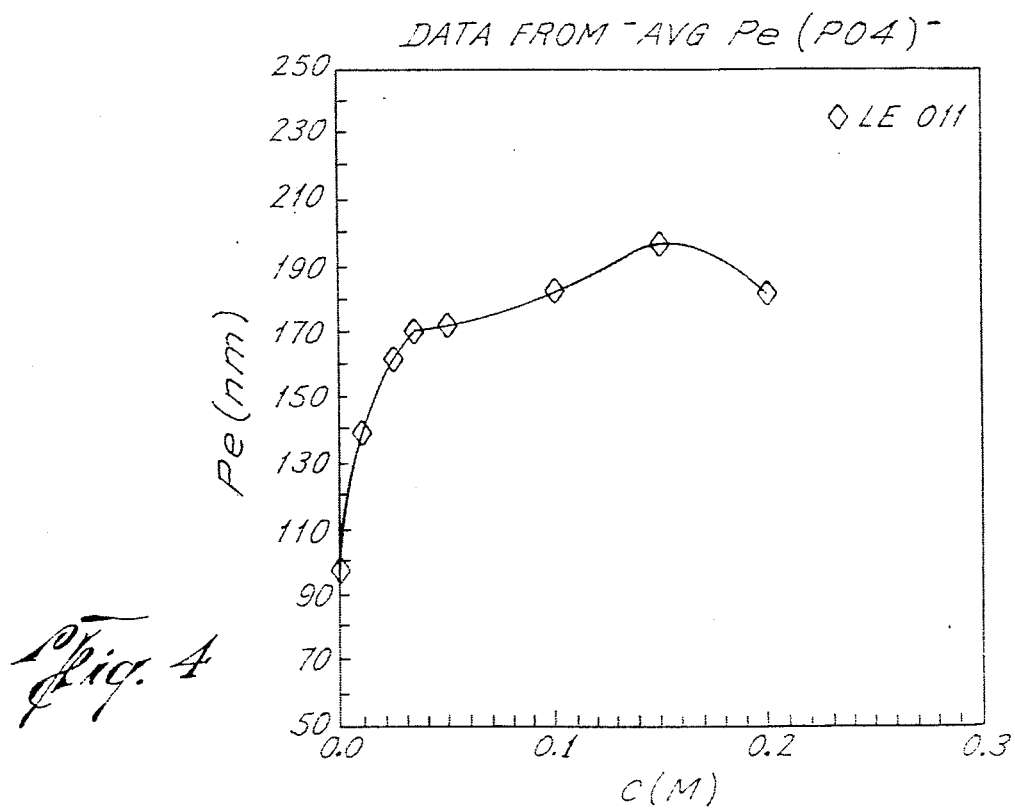
FIG. 4 is a graphic representation of increasing pore size (Pe) as the concentration of buffer increases. These sizes were determined by the procedure of G. A. Griess, 28, 1475-1484.

It has been determined that as the molar concentration of the buffer increases, the pore size progressively increases. This phenomenon continues, until, at one point, a high enough buffer concentration will either not effect pore size or will actually begin decreasing pore size. According to one experiment conducted by the present inventors, pore size progressively increased as the concentration of a phosphate buffer (pH 7.4) increased until it reached 0.15 M. It was also noted that as phosphate buffer concentrations increased above 0.15 M, pore size decreased. This phenomenon is also demonstrated in FIG. 4. FIG. 4 shows that as the concentration of salt (NaCl) decreased below 0.15 M, the agarose gel pore size decreased.

Another embodiment of the present invention is directed to a process for producing an agarose gel in a vertical gel mold having a uniform agarose concentration and a pore size gradient. The process includes several steps. One step is preparing a plurality of buffered aqueous agarose solutions. Each of the solutions includes an identical concentration of agarose and a different molar concentration of buffer.

According to one preferred embodiment, a plurality of buffered agarose solutions is prepared by a process including the steps of: (a) preparing an aqueous agarose solution; (b) subdividing the aqueous agarose solution into a plurality of containers; (c) adding, prior to gelation, a different molar concentration of a buffer to each container of aqueous agarose solution. Any desired number of buffered aqueous agarose solutions may be prepared in this manner.

The concentrations of agarose included in the buffered aqueous agarose solutions is preferably from about 0.5% to about 5% (w/v), and most preferably from about 1% to about 3% (w/v). The concentration of buffer and/or salt added to each aqueous solution of agarose may generally be from about 0.000 M to about 0.5 M, and most preferably from about 0.01 M to about 0.05 M.

According to this embodiment, another step in the inventive process is adding, sequentially, in order of decreasing buffer or salt concentration, the agarose aqueous solutions to a vertical gel mold prior to gelation. According to one preferred embodiment, each buffered aqueous agarose solution is added only after the previously added solution has gelled in the vertical gel mold. When adding in order of decreasing salt or buffer concentration, the ultimate gel pore size decreases as buffer concentration decreases so that the gels would be eventually inverted for sample application. The differences among the specific gravities of the agarose solutions must be sufficient to prevent convective disturbance.

The pore size gradiated agarose gels of the present invention are useful for several sieving-based techniques. An agarose gel having a gradient of pore size (Pe or PE) may be utilized in a technique to separate molecules by molecular weight. Accordingly, molecules of various molecular weights would be added to the agarose gel at the site of greatest pore size. The molecules are driven through the agarose gel. Ultimately, the differing molecules are restricted by the pore size of the gel. Once the motion of the molecules through the agarose gel is complete, or after a predetermined amount of time, separation of the molecules is concluded.

Another embodiment of the present invention is directed to a process for producing an agarose gel having a uniform agarose concentration and a pore size gradient in a horizontal gel mold. The process includes several steps. One step is dividing the horizontal gel mold into a first and second compartment. This may be accomplished in any manner which substantially divides the horizontal gel mold into at least two compartments. Most preferably, the compartment which will later contain the agarose solution at a higher buffer concentration is the smaller of the two compartments.

According to a preferred aspect of the present invention, an agarose gel of the present invention having a pore size gradient is utilized for an electrophoresis technique. After formation of a gel with a pore size gradient by gelation at varying buffer/salt concentrations, the buffer and/or salt may preferably be removed and replaced by a selected buffer appropriate for the electrophoresis process. Accordingly, particles of various weights, sizes, charges and/or shapes are added to the agarose gel at a site of greatest pore size and electrophoresis is then performed. During electrophoresis, the molecules migrate through the gel, progressively slowing as pore size decreases. The pore size gradient thus sharpens the bands formed by particles that have given characteristics of size, charge and shape. It also increases the range of particles that can be separated on one gel. The particles can be any charged particle of appropriate size, including protein, DNA and RNA.

In this aspect of the present invention a non-buffered aqueous agarose solution may be used in combination with a buffered agarose solution. The non-buffered aqueous agarose solution is prepared in substantially the same manner as set forth above in previous embodiments of the present invention. The non-buffered aqueous agarose solution is then poured into the remaining compartment of the horizontal gel mold prior to gelation. It should be noted that the dividing means may be left in place until the non-buffered aqueous agarose solution has been added and then removed. Once the non-buffered aqueous agarose solution is in contact with the gelled buffered aqueous agarose gel, the buffer will diffuse throughout the non-buffered aqueous agarose solution, and upon gelation the non-buffered aqueous agarose solution will contain a buffer concentration gradient. The buffer concentration decreases as the distance from the buffered aqueous agarose gel increases. Thus, upon gelation of the non-buffered aqueous agarose solution, pore size will decrease as the distance from the buffered-aqueous gel increases. Accordingly, a gradient of pore size is created.

The following example is presented to describe preferred embodiments and utilities of the present invention and is not meant to limit the present invention unless otherwise stated in the claims appended hereto.

EXAMPLE

A horizontal pore gradient gel that has the same concentration of agarose throughout was prepared by the following procedure:

A strip of agarose was cast in comparatively high ionic strength buffer, 0.5 M NaCl (salt) in one compartment (high salt) of a horizontal electrophoresis apparatus strip was restricted in width by a PLEXIGLAS bar placed in the gel bed to divide the high salt from the no salt compartment.

Figure 1:
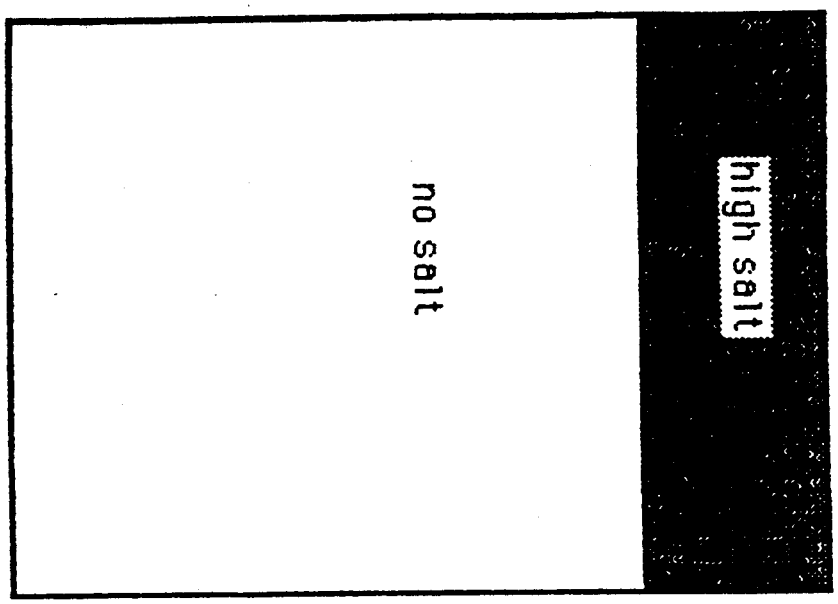
FIG. 1 is an illustration of a horizontal gel mold in which the first and second compartments are identified; the first compartment for containing a first aqueous agarose solution; the second compartment for containing a second aqueous agarose solution.
Figure 2:
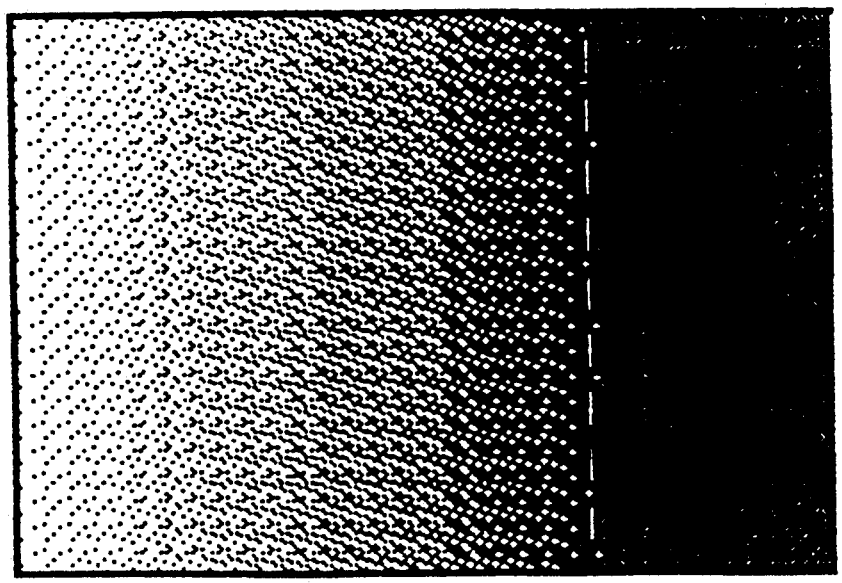
FIG. 2 illustrates the diffusion of the buffer throughout the aqueous non-buffered agarose solution.
Figure 3:
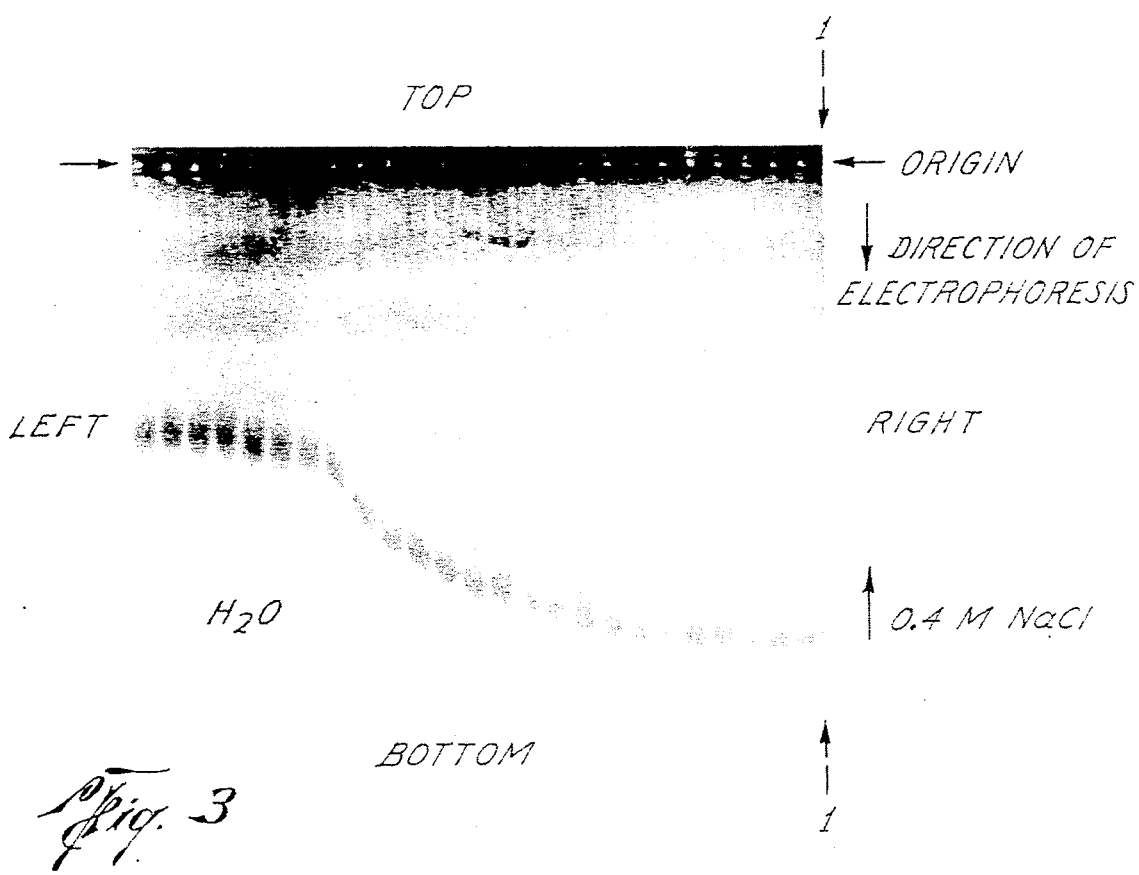
FIG. 3 is a photograph of an agarose gel having a gradient of pore size after horizontal electrophoresis of latex spheres was completed. The latex spheres electrophoresed moved from top to bottom. The buffer concentration during gelation increased from left to right.

The bar was removed after the buffered agarose had gelled. A sample well-forming comb was placed in the gel bed, as is conventionally done. An aqueous agarose solution was prepared. The aqueous agarose solution included 1% agarose, and was prepared in water having a temperature of 60° C. The aqueous agarose solution was then, prior to gelation, poured into the remaining compartment (no salt) of the gel bed. At one end, the molten NaCl. During its gelation, the molten unbuffered aqueous agarose developed a horizontal NaCl gradient because of the diffusion of NaCl from the gelled agarose. When the molten aqueous agarose solution gelled, the NaCl gradient produce a Pe (pore size) gradient (data in FIG. 4). FIG. 4 shows how (Pe) decreased as buffer concentration decreased below 0.15 M. It should alwo be noted that pore size begins to decrease above about 0.15 M. This phenomenon could lead to pore size gradients formed with pore sizes decreasing as salt or buffer concentrations increase above about 0.15 M. agarose (LE 62677) by the following procedure. Agarose in 0.4 M NaCl was placed in lane 1 and allowed to gel. The rest of the mold was then filled with 1% agarose free of buffer and salt. Gelation of the latter agarose was extended for about one hour by exposure to a heat lamp, during which salt from the first gel diffused across. A set of sample wells was formed across the gradient from right to left with a comb at one end of the gel bed (See FIG. 3). Negatively charged latex spheres (11 micron diameter) were loaded in the sample wells (the wells all had the same sample of latex spheres). The gel was soaked overnight in 0.0253 M sodium phosphate, pH 7.4, 0.0013 M $MgCl_2$ and 0.5% TRITON X-100 before use. The TRITON X-100 is a non-ionic detergent present to prevent sticking of the latex spheres to the gel. Electrophoresis was performed in 0.025 M sodium phosphate, pH 7.4, 0.001 M $MgCl_2$, 0.5% TRITON X-100. After electrophoresis, the latex spheres were detected by their light scattering and found to migrate a distance that decreased with distance from the position of the original contact with the NaCl-containing gel (FIG. 3). This contact is indicated in FIG. 3 as contact line (1→). The spheres migrated from top to bottom. In FIG. 3 the spheres nearest the line of contract, migrated the furthest, as predicted from the expected finding of the highest Pe nearest the line of contact. That is, during gelation the highest salt concentration was located near the line of contact. This experiment demonstrates validity of the present invention. It should be noted, however, that in most instances the direction of electrophoresis would be along the gradient rather than across it as shown here.

The references cited in the above text are incorporated in pertinent part herein for the reasons cited.

Changes may be made in the components and assemblies described herein or in the steps or the sequence of steps of the method described herein without departing from the concept and scope of the invention as defined in the following claims.

What is claimed is:

1. A method for controlling the pore size of an agarose gel, the method including the steps of:
   (a) preparing an aqueous solution of agarose; and
   (b) adding said aqueous solution of agarose to a mold with a concentration gradient of at least one of a salt or buffer; and
   (c) gelling the agarose, said concentration gradient determining pore size of subsequently gelled agarose.

2. A method for preparing an agarose gel having a pore size gradient, the method comprising the steps of:

(a) placing at least one aqueous solution of agarose in a gel bed mold having a first end and a second end so that a salt or buffer concentration gradient in said emplaced solution increases from the second end to the first end; and (b) allowing said placed aqueous solution to gel to achieve an agarose gel having a pore size gradient, the pore size increasing from the first end to the second end.

3. The method of claim 1 or 2 wherein the agarose in said aqueous solution is at a concentration of from about 0.5% to about 5% (w/v).

4. The method of claim 1 or 2 wherein the agarose is at a concentration in said aqueous solution of from about 1% to about 2% (w/v).

5. The method of claim 1 or 2 wherein the molar concentration gradient of said salt or buffer is in a range between about 0.00 M and about 0.5 M.

6. The method of claim 1 or 2 wherein the molar concentration gradient of said salt or buffer ranges from about 0.01 M to about 0.05 M.

7. The method of claims 1 or 2 wherein said salt or buffer comprises at least one of potassium dihydrogen phosphate, disodium hydrogen phosphate, tris-(hydroxymethyl)aminomethane, sodium bicarbonate, sodium acetate, sodium tetraborate, sodium chloride, potassium chloride and calcium chloride.

8. A method for controlling pore size of an agarose gel, the method including the steps of:
   (a) preparing a 1% aqueous solution of agarose; and
   (b) adding to said aqueous solution of agarose a concentration gradient of disodium hydrogen phosphate of from about 0.01 M to about 0.5 M moles, the molar concentration of disodium hydrogen phosphate determining pore size upon gelation.

9. A process for producing an agarose gel having a uniform agarose concentration and a pore size gradient in a vertical gel mold, comprising the steps of:
   (a) preparing a plurality of buffered aqueous agarose solutions, each solution including an identical concentration of agarose (w/v) and a different concentration of a salt or buffer, said salt or buffer concentration determining pore size of the agarose upon gelation;
   (b) layering at least a portion of each solution in a gel mold; and
   (c) allowing gelation to occur.

10. The process of claim 9 wherein the agarose in said aqueous solutions is from about 0.5% to about 5% (w/v).

11. The process of claim 9 wherein the agarose in said aqueous solutions is from about 1% to about 2% (w/v).

12. The process of claim 9 wherein said salt or buffer is at a concentration of from about 0.005 to about 0.5 M.

13. The process of claim 9 wherein said salt or buffer is at a concentration of from about 0.00 to about 0.05 M.

14. The process of claims 9, 12 or 13 wherein said salt or buffer comprises at least one of potassium dihydrogen phosphate, disodium hydrogen phosphate, tris-(hydroxymethyl)aminomethane, sodium bicarbonate, sodium acetate, sodium tetraborate, potassium chloride, calcium chloride and sodium chloride.

15. The process of claim 9 wherein said buffered solutions are added to said vertical gel mold successively, in order of decreasing buffer or salt concentrations.

16. The process of claim 9 wherein said buffered solutions are added to said vertical gel mold successively in order of decreasing salt or buffer concentration.

17. A process for producing an agarose gel having a pore size gradient in a vertical gel mold, the process comprising the steps of:
   (a) preparing a plurality of aqueous agarose solutions, each solution including a different molar concentration of a salt or buffer;
   (b) layering, sequentially in order of decreasing salt or buffer concentration, the aqueous agarose solutions in a vertical gel mold; and
   (c) allowing the agarose in the gel mold to gel.

18. The process of claim 17 wherein the agarose in said aqueous solutions is at a concentration of from about 0.5% to about 5% (w/v).

19. The process of claim 17 wherein the agarose in said aqueous solutions is at a concentration of from about 1% to about 2% (w/v).

20. The process of claim 17 wherein the molar concentration of said buffer or salt is from about 0.005 M to about 0.5 M.

21. The process of claim 17 wherein the concentration of said buffer or salt is from about 0.00 M to about 0.05 M.

22. The process of claims 17, 19 or 20 wherein said salt or buffer comprises at least one of potassium dihydrogen phosphate, disodium hydrogen phosphate, tris-(hydroxymethyl)aminomethane, sodium bicarbonate, sodium acetate, sodium tetraborate, potassium chloride, calcium chloride or sodium chloride.

23. A sieving-based method of separating molecules of various sizes, shapes and molecular weights, the method comprising the steps of:
   (a) preparing a plurality of aqueous agarose solutions, each solution including a different concentration of a salt or buffer;
   (b) adding to a vertical gel mold, said aqueous agarose solutions in order of decreasing salt or buffer molar concentration;
   (c) gelling agarose in the mold;
   (d) introducing molecules to be separated into the gelled agarose; and
   (e) separating said molecules, thereafter, by a sieving-based technique.

24. The method of claim 23 wherein the concentration of agarose in said aqueous solutions is from about 0.5% to about 5% (w/v).

25. The method of claim 23 wherein the concentration of agarose in said aqueous solutions is from about 1% to about 2% (w/v).

26. The method of claim 23 wherein the concentration of said salt or buffer is from about 0.005 M to about 0.5 M.

27. The method of claim 23 wherein the concentration of said salt or buffer is from about 0.00 M to about 0.05 M.

28. The method of claims 23, 26 or 27 wherein said salt or buffer comprises at least one of potassium dihydrogen phosphate, disodium hydrogen phosphate, tris-(hydroxymethyl)aminomethane, sodium bicarbonate, sodium acetate, sodium tetraborate, potassium chloride, calcium chloride and sodium chloride.

29. The method of claim 23 wherein said molecules to be separated include at least one type of protein, DNA fragment or RNA fragment.

30. The method of claim 23 wherein said sieving-based technique is electrophoresis.

31. An agarose gel for separating molecules of various molecular weights, sizes and shapes, by sieving, said agarose gel having a uniform agarose concentration (w.v/) and a gradient of pore size, said agarose gel being produced by the process comprising the steps of:
(a) preparing a plurality of aqueous agarose solutions, each solution including an identical concentration of agarose (w/v) and a different concentration of a salt or buffer; and
(b) layering said aqueous agarose solutions in a vertical gel mold in order of decreasing buffer or salt concentration.

32. The agarose gel of claim 31 wherein the agarose in said aqueous solutions is at a concentration of from about 0.5% to about 5% (w/v).

33. The agarose gel of claim 31 wherein the agarose in said aqueous solutions is at a concentration of from about 1% to about 2% (w/v).

34. The agarose gel of claim 31 wherein the concentration of salt or buffer is from about 0.005 M to about 0.5 M.

35. The agarose gel claim 31 wherein the concentration of said salt or buffer is from about 0.00 M to about 0.05 M.

36. The agarose gel of claims 31, 34 or 35 wherein said salt or buffer comprises at least one of potassium dihydrogen phosphate, disodium hydrogen phosphate, tris(hydroxymethyl)aminomethane, sodium bicarbonate, sodium acetate, sodium tetraborate, calcium chloride, potassium chloride and sodium chloride.

37. An agarose gel having a uniform agarose concentration (w/v) and a pore size gradient for separating biological molecules of various molecular weight, size and shape by sieving during electrophoresis and produced by the process comprising the steps of:
(a) preparing a plurality of disodium hydrogen phosphate buffered aqueous agarose solutions, each solution including an identical concentration of from 0.5% to about 5% (w/v) agarose and a different disodium hydrogen phosphate concenand
(b) adding to a vertical gel mold, said disodium hydrogen phosphate-buffered aqueous agarose solutions in order of decreasing disodium hydrogen phosphate concentration.

38. A process for producing an agarose gel having a uniform agarose concentration and a pore size gradient in a horizontal gel mold, the process comprising the steps
(a) dividing a horizontal gel mold into a first and second compartment by dividing means;
(b) preparing a first aqueous agarose solution having a first buffer or salt concentration;
(c) pouring said first aqueous agarose solution into said first compartment;
(d) removing, after gelation of said first aqueous agarose solution said dividing means;
(e) preparing a second aqueous agarose solution said second aqueous agarose solution having a lower buffer or salt concentration than the first agarose solution;
(f) pouring said second aqueous agarose solution into said second compartment;
(g) allowing diffusion of salt or buffer from the gelled first agarose solution into the second solution to form a salt or buffer concentration gradient in the second solution; and
(h) gelling said second agarose aqueous solution.

39. The process of claim 38 wherein the agarose in said second aqueous solution is at a concentration of from about 0.5% to about 5% (w/v).

40. The process of claim 38 wherein the agarose in said first aqueous solution and said second aqueous agarose solution is at a concentration of from about 1% to about (w/v).

41. The process of claim 38 wherein the salt or buffer in said first aqueous agarose solution is at a concentration of from about 0.15 M to about 0.5 M.

42. The process of claim 38 wherein the molar concentration of said salt or buffer in said concentration gradient is from about 0.00 M to about 0.15 M.

43. The process of claims 38, 41 or 42 wherein said salt or buffer is at least one of potassium dihydrogen phosphate, disodium hydrogen phosphate, tris-(hydroxymethyl)aminomethane, sodium bicarbonate, sodium acetate, sodium tetraborate, calcium chloride, potassium chloride, and sodium chloride.

44. A method of separating molecules of various molecular weights, sizes and shapes by a sieving-based technique, the method comprising the steps of:
(a) dividing a horizontal gel mold into a first and second compartment by dividing means;
(b) preparing a first aqueous agarose solution comprising a first concentration buffer or salt;
(c) pouring said first aqueous agarose solution into said first compartment;
(d) removing said dividing means after gelation of said first aqueous agarose solution;
(e) preparing a second aqueous agarose solution; and
(f) pouring said second aqueous agarose solution into said second compartment and gelling said second aqueous agarose solution;
(g) introducing molecules to be separated into or in proximity to the first gelled agarose; and
(h) separating said molecules, thereafter, by a sieving-based technique.

45. The method of claim 44 wherein the agarose in said first and second aqueous agarose solution is at a concentration of from about 0.5% to about 5% (w/v).

46. The method of claim 44 wherein the agarose in said first and second aqueous agarose solutions is at a concentration of from about 1% to about 2% (w/v).

47. The method of claim 44 wherein the salt or buffer in said first aqueous agarose solution is at a concentration of from about 0.005 M to about 0.5 M.

48. The method of claim 44 wherein the salt or buffer in said first aqueous agarose solution is at a concentration of from about 0.01 M to about 0.15 M.

49. The method of claims 44, 47 or 48 wherein said salt or buffer is at least one of potassium dihydrogen phosphate, disodium hydrogen phosphate, tris-(hydroxymethyl)aminomethane, sodium bicarbonate, sodium acetate, sodium tetraborate, potassium chloride, calcium chloride and sodium chloride.

50. The method of claim 44 wherein said molecules are at least one type of molecule selected from the group consisting of proteins, DNA fragments and RNA fragments.

51. The method of claim 44 wherein said sieving-based technique is electrophoresis.

52. An agarose gel for separating molecules of various molecular weights by a sieving-based technique, said agarose gel having a gradient of pore size and being produced by a process comprising the steps of:
(a) dividing a horizontal gel mold into a first and second compartment by dividing means;

(b) preparing a first aqueous agarose solution comprising a first concentration of buffer or salt;

(c) pouring said first aqueous agarose solution into said first compartment;

(d) removing said dividing means after gelation of said first aqueous solution of agarose;

(e) preparing a second aqueous agarose solution free of buffer or salt or having a second concentration of buffer or salt less than the first concentration;

(f) pouring said second aqueous agarose solution into said second compartment;

(g) permitting diffusion of buffer or salt from the first gelled agarose into the second agarose solution to form a salt or buffer concentration gradient; and (h) allowing said second aqueous agarose solution to gel.

53. The agarose gel of claim 52 wherein the agarose in said first aqueous solution and said second aqueous agarose solution is at a concentration of from about 0.5% to about 5% (w/v).

54. The agarose gel of claim 52 wherein the agarose in said first aqueous agarose solution and said second aqueous agarose solution is at a concentration of from about 1 to about 2% (w/v).

55. The agarose gel of claim 52 wherein the salt or buffer in said first aqueous agarose solution is at a concentration of from about 0.15 M to about 0.5 M.

56. The agarose gel claim 52 wherein the salt or buffer in said first aqueous agarose solution is at a concentration of from about 0.1 M to about 0.5 M.

57. The agarose gel of claims 52, 55 or 56 wherein said salt or buffer comprises at least one of potassium dihydrogen phosphate, disodium hydrogen phosphate, tris(hydroxymethyl)aminomethane, sodium bicarbonate, sodium acetate, sodium tetraborate, potassium chloride, calcium chloride, and sodium chloride.

58. An agarose gel having a uniform agarose concentration and a gradient of pore size for separating biological molecules by sieving-based electrophoresis said gel being produced by a process comprising the steps of:

(a) dividing a horizontal gel mold into a first and second compartment by dividing means;

(b) preparing an aqueous 0.5 M sodium chloride agarose solution, said solution including 1% (w/v) agarose;

(c) pouring said solution into said first compartment;

(d) removing, after gelation of said solution, said dividing means;

(e) preparing a salt and buffer-free aqueous agarose solution, said salt and buffer-free aqueous agarose solution including 1% (w/v) agarose; and (f) pouring said salt and buffer-free aqueous agarose solution into said second compartment; and (g) gelling agarose in said salt and buffer-free solution.

59. An agarose gel slab having a first end, a second end, a uniform agarose concentration and a gradient of pore size from the first end to the second end.

* * * * *

UNITED STATES PATENT AND TRADEMARK OFFICE
CERTIFICATE OF CORRECTION

PATENT NO.    : 5,009,759
DATED         : April 23, 1991
INVENTOR(S)   : Philip Serwer; Gary A. Griess, San Antonio, Texas It is certified that error appears in the above-identified patent and that said Letters Patent is hereby corrected as shown below:

Claim 31, line 4, column 11, delete "(w.v/)" and replace with --(w/v)--.

Claim 35, line 22, column 11, insert --of-- between 'gel' and 'claim'.

Claim 37, line 41, column 11, delete "concenand" and replace with --concentration of from about 0.01M to about 0.05M; and--

Claim 38, line 49, column 11, insert --of:-- after 'steps'.

Claim 38, line 57, column 11, insert --,-- after the word 'solution'.

Claim 38, line 58, column 11, insert --,-- after the word 'solution'.

UNITED STATES PATENT AND TRADEMARK OFFICE
CERTIFICATE OF CORRECTION

PATENT NO. : 5,009,759

DATED : April 23, 1991

INVENTOR(S) : Philip Serwer; Gary A. Griess, San Antonio Texas

Page 2 of 2

It is certified that error appears in the above-identified patent and that said Letters Patent is hereby corrected as shown below:

Claim 40, line 7, column 12, add --2%-- between "about and "(w/v)".

Claim 56 line 1, column 14, insert --of-- between "gel" and "claim".

Claim 58, line 12, column 14, insert --,-- after the word "electrophoresis".

Signed and Sealed this

Tenth Day of November, 1992

Attest:

DOUGLAS B. COMER

Attesting Officer

Acting Commissioner of Patents and Trademarks